(12) United States Patent
Olson et al.

(10) Patent No.: US 10,292,711 B2
(45) Date of Patent: May 21, 2019

(54) MITRAL VALVE TREATMENT DEVICE HAVING LEFT ATRIAL APPENDAGE CLOSURE

(71) Applicant: St. Jude Medical, Cardiology Division, Inc., St. Paul, MN (US)

(72) Inventors: Richard J. Olson, Blaine, MN (US); Tracee Eidenschink, Wayzata, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 198 days.

(21) Appl. No.: 14/602,471

(22) Filed: Jan. 22, 2015

(65) Prior Publication Data

US 2015/0223820 A1    Aug. 13, 2015

Related U.S. Application Data

(60) Provisional application No. 61/937,000, filed on Feb. 7, 2014.

(51) Int. Cl.
*A61B 17/12* (2006.01)
*A61F 2/24* (2006.01)
*A61B 17/00* (2006.01)

(52) U.S. Cl.
CPC .. *A61B 17/12122* (2013.01); *A61B 17/12168* (2013.01); *A61B 17/12172* (2013.01); *A61F 2/2412* (2013.01); *A61F 2/2418* (2013.01); *A61F 2/2445* (2013.01); *A61B 2017/00867* (2013.01); *A61B 2017/1205* (2013.01); *A61F 2/2436* (2013.01); *A61F 2/2466* (2013.01); *A61F 2220/0075* (2013.01)

(58) Field of Classification Search
CPC ................ A61F 2/2445; A61F 2/2448; A61B 17/12118; A61B 17/12122; A61B 17/12172
See application file for complete search history.

(56) References Cited

U.S. PATENT DOCUMENTS

| 3,657,744 A | 4/1972 | Ersek |
| 4,275,469 A | 6/1981 | Gabbay |
| 4,423,730 A | 1/1984 | Gabbay |
| 4,491,986 A | 1/1985 | Gabbay |

(Continued)

FOREIGN PATENT DOCUMENTS

| DE | 19857887 A1 | 7/2000 |
| DE | 10121210 A1 | 11/2002 |

(Continued)

OTHER PUBLICATIONS

Catheter-implanted prosthetic heart valves, Knudsen, L.L., et al., The International Journal of Artificial Organs, vol. 16, No. 5 1993, pp. 253-262.

(Continued)

*Primary Examiner* — Alexander J Orkin
(74) *Attorney, Agent, or Firm* — Lerner, David, Littenberg, Krumholz & Mentlik, LLP

(57) ABSTRACT

A heart treatment device includes an annuloplasty ring for restoring function to a mitral valve, an occluder configured and arranged for implantation within a left atrial appendage and a connector interconnecting the annuloplasty ring and the occluder.

11 Claims, 13 Drawing Sheets

(56) References Cited

U.S. PATENT DOCUMENTS

| | | | |
|---|---|---|---|
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,480,423 A | 1/1996 | Ravenscroft et al. | |
| 5,843,167 A | 12/1998 | Dwyer et al. | |
| 5,855,601 A | 1/1999 | Bessler et al. | |
| 5,924,424 A | 7/1999 | Stevens et al. | |
| 5,935,163 A | 8/1999 | Gabbay | |
| 5,961,549 A | 10/1999 | Nguyen et al. | |
| 5,968,068 A | 10/1999 | Dehdashtian et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,231,561 B1* | 5/2001 | Frazier | A61B 17/00234 604/500 |
| 6,264,691 B1 | 7/2001 | Gabbay | |
| 6,267,783 B1 | 7/2001 | Letendre et al. | |
| 6,306,141 B1 | 10/2001 | Jervis | |
| 6,332,893 B1* | 12/2001 | Mortier | A61F 2/2454 623/2.1 |
| 6,368,348 B1 | 4/2002 | Gabbay | |
| 6,419,695 B1 | 7/2002 | Gabbay | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,374,573 B2 | 5/2008 | Gabbay | |
| 7,381,218 B2 | 6/2008 | Schreck | |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,914,569 B2 | 3/2011 | Nguyen et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| 2002/0036220 A1 | 3/2002 | Gabbay | |
| 2003/0023303 A1 | 1/2003 | Palmaz | |
| 2003/0050682 A1* | 3/2003 | Sharkey | A61B 17/12022 607/126 |
| 2003/0050694 A1 | 3/2003 | Yang et al. | |
| 2003/0130726 A1 | 7/2003 | Thorpe | |
| 2004/0049262 A1 | 3/2004 | Obermiller et al. | |
| 2004/0093075 A1 | 5/2004 | Kuehne | |
| 2004/0210304 A1 | 10/2004 | Seguin et al. | |
| 2004/0260393 A1* | 12/2004 | Rahdert | A61B 17/00234 623/2.36 |
| 2005/0055089 A1* | 3/2005 | Macoviak | A61F 2/2445 623/2.37 |
| 2005/0096726 A1 | 5/2005 | Sequin et al. | |
| 2005/0137695 A1 | 6/2005 | Salahieh et al. | |
| 2005/0137697 A1 | 6/2005 | Salahieh et al. | |
| 2005/0222488 A1* | 10/2005 | Chang | A61B 17/00234 600/37 |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0106415 A1 | 5/2006 | Gabbay | |
| 2006/0122692 A1 | 6/2006 | Gilad et al. | |
| 2006/0142848 A1 | 6/2006 | Gabbay | |
| 2006/0149360 A1 | 7/2006 | Schwammenthal et al. | |
| 2006/0167468 A1 | 7/2006 | Gabbay | |
| 2006/0173532 A1 | 8/2006 | Flagle et al. | |
| 2006/0178740 A1 | 8/2006 | Stacchino et al. | |
| 2006/0195183 A1* | 8/2006 | Navia | A61F 2/2409 623/2.18 |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0073391 A1 | 3/2007 | Bourang et al. | |
| 2007/0083232 A1* | 4/2007 | Lee | A61B 17/0057 606/213 |
| 2007/0088431 A1 | 4/2007 | Bourang et al. | |
| 2007/0093890 A1 | 4/2007 | Eliasen et al. | |
| 2007/0100435 A1 | 5/2007 | Case et al. | |
| 2007/0112422 A1 | 5/2007 | Dehdashtian | |
| 2007/0118210 A1 | 5/2007 | Pinchuk | |
| 2007/0156233 A1* | 7/2007 | Kapadia | A61F 2/2409 623/2.11 |
| 2007/0162100 A1 | 7/2007 | Gabbay | |
| 2007/0168013 A1 | 7/2007 | Douglas | |
| 2007/0203575 A1 | 8/2007 | Forster et al. | |
| 2007/0213813 A1 | 9/2007 | Von Segesser et al. | |
| 2007/0233228 A1 | 10/2007 | Eberhardt et al. | |
| 2007/0239271 A1 | 10/2007 | Nguyen | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147182 A1 | 6/2008 | Righini et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0054975 A1 | 2/2009 | del Nido et al. | |
| 2009/0099596 A1* | 4/2009 | McGuckin, Jr. | A61B 17/0057 606/216 |

(56) References Cited

U.S. PATENT DOCUMENTS

| | | | |
|---|---|---|---|
| 2009/0112249 A1* | 4/2009 | Miles | A61B 17/12122 606/192 |
| 2009/0112309 A1 | 4/2009 | Jaramillo et al. | |
| 2009/0138079 A1 | 5/2009 | Tuval et al. | |
| 2010/0004740 A1 | 1/2010 | Seguin et al. | |
| 2010/0036484 A1 | 2/2010 | Hariton et al. | |
| 2010/0049306 A1 | 2/2010 | House et al. | |
| 2010/0087907 A1 | 4/2010 | Lattouf | |
| 2010/0121435 A1* | 5/2010 | Subramanian | A61F 2/2445 623/2.11 |
| 2010/0131055 A1 | 5/2010 | Case et al. | |
| 2010/0168778 A1 | 7/2010 | Braido | |
| 2010/0168839 A1 | 7/2010 | Braido et al. | |
| 2010/0185277 A1 | 7/2010 | Braido et al. | |
| 2010/0191326 A1 | 7/2010 | Alkhatib | |
| 2010/0204781 A1 | 8/2010 | Alkhatib | |
| 2010/0204785 A1 | 8/2010 | Alkhatib | |
| 2010/0217382 A1 | 8/2010 | Chau et al. | |
| 2010/0249911 A1 | 9/2010 | Alkhatib | |
| 2010/0249923 A1 | 9/2010 | Alkhatib et al. | |
| 2010/0280606 A1* | 11/2010 | Naor | A61F 2/2418 623/2.18 |
| 2010/0286768 A1 | 11/2010 | Alkhatib | |
| 2010/0298931 A1 | 11/2010 | Quadri et al. | |
| 2011/0029072 A1 | 2/2011 | Gabbay | |
| 2011/0224678 A1 | 9/2011 | Gabbay | |
| 2012/0197388 A1* | 8/2012 | Khairkhahan | A61F 2/246 623/2.11 |
| 2012/0245678 A1* | 9/2012 | Solem | A61M 1/1081 623/2.36 |
| 2012/0283585 A1* | 11/2012 | Werneth | A61B 17/0057 600/508 |
| 2014/0031928 A1* | 1/2014 | Murphy | A61B 17/0057 623/2.18 |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1129744 A1 | 9/2001 |
| EP | 1157673 A2 | 11/2001 |
| EP | 1360942 A1 | 11/2003 |
| EP | 1584306 A1 | 10/2005 |
| EP | 1598031 A2 | 11/2005 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 0149213 A2 | 7/2001 |
| WO | 01054625 A1 | 8/2001 |
| WO | 01056500 A2 | 8/2001 |
| WO | 01076510 A2 | 10/2001 |
| WO | 0236048 A1 | 5/2002 |
| WO | 0247575 A2 | 6/2002 |
| WO | 03047468 A1 | 6/2003 |
| WO | 06073626 A2 | 7/2006 |
| WO | 07071436 A2 | 6/2007 |
| WO | 08070797 A2 | 6/2008 |
| WO | 10008548 A2 | 1/2010 |
| WO | 10008549 A1 | 1/2010 |
| WO | 10051025 A1 | 5/2010 |
| WO | 10087975 A1 | 8/2010 |
| WO | 10096176 A1 | 8/2010 |
| WO | 10098857 A1 | 9/2010 |

OTHER PUBLICATIONS

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

Percutaneous aortic valve replacement: resection before implantation, 836-840, Quaden, Rene et al., European J. of Cardio-thoracic Surgery, 27 (2005).

Ruiz, Carlos, "Overview of PRE-CE Mark Transcatheter Aortic Valve Technologies", Euro PCR, May 25, 2010.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology (1998) 7:102-106.

Transluminal implantation of artificial heart valves, Andersen, H. R., et al., European Heart Journal (1992) 13, 704-708.

U.S. Appl. No. 29/375,243, filed Sep. 20, 2010.

U.S. Appl. No. 29/375,260, filed Sep. 20, 2010.

* cited by examiner

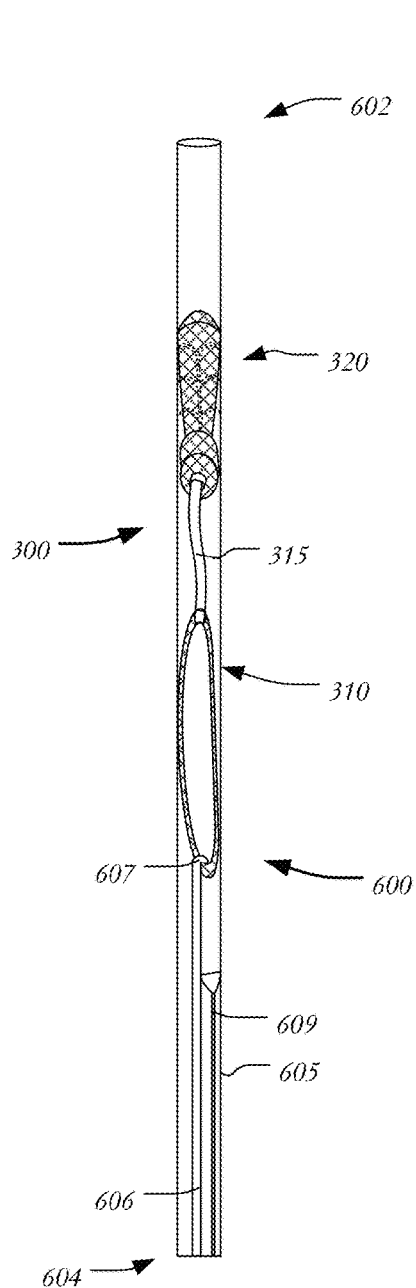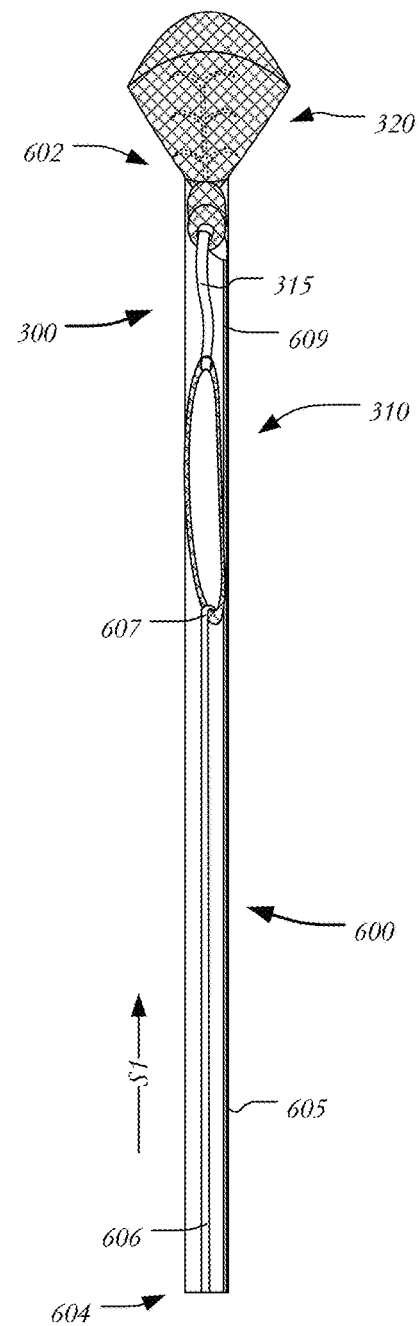
FIG. 6B                    FIG. 6C

MITRAL VALVE TREATMENT DEVICE HAVING LEFT ATRIAL APPENDAGE CLOSURE

CROSS-REFERENCE TO RELATED APPLICATIONS

The present application claims the benefit of the filing date of U.S. Provisional Patent Application No. 61/937,000 filed Feb. 7, 2014, the disclosure of which is hereby incorporated herein by reference.

BACKGROUND OF THE INVENTION

The present invention relates to heart valve treatment and, in particular, to mitral valve leaflet repair and left atrial appendage closure. More particularly, the present invention relates to devices and methods for treating both the mitral valve and the left atrial appendage.

Properly functioning heart valves can maintain unidirectional blood flow in the circulatory system by opening and closing, depending on the difference in pressure from one side of the valve to the other. The two atrioventricular valves (mitral and tricuspid valves) are multicusped valves that prevent backflow from the ventricles into the atria during systole. They are anchored to the wall of the ventricle by chordae tendineae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). In one example, the chordae tendineae may stretch and thus become too long, or the chordae tendineae may be ruptured. As a result, the valve does not close normally and the unsupported valve leaflet may bulge back, or "prolapse," into the left atrium like a parachute. Thus, as the ventricle contracts, the abnormal leaflet may be propelled backwards, beyond its normal closure line and into the left atrium, thereby allowing blood to return to the left atrium and the lungs.

Mitral valve prolapse causes mitral regurgitation. Isolated posterior leaflet prolapse of the human heart mitral valve, i.e., prolapse of a single leaflet, is the most common cause of mitral regurgitation. The exact cause of the prolapse may not be clear. Untreated mitral regurgitation may lead to congestive heart failure and pulmonary hypertension.

Located near the mitral valve is the left atrial appendage, a small pouch which empties into the left atrium. Under certain conditions, the heart may contract in an abnormal manner. When this happens, as will be explained in greater detail below, the left atrial appendage may be responsible for clot formation, which may cause a stroke.

There therefore is a need for further improvements to the current techniques for heart valve leaflet repair and/or replacement while minimizing the risk of stroke associated with the left atrial appendage. Among other advantages, the present invention may address one or more of these needs.

SUMMARY OF THE INVENTION

In some embodiments, a heart treatment device includes an annuloplasty ring for maintaining or restoring function to a mitral valve, an occluder configured and arranged for implantation within a left atrial appendage and a connector interconnecting the annuloplasty ring and the occluder.

In some embodiments, a heart treatment device includes a prosthetic heart valve including a stent, a cuff disposed about the stent and a plurality of leaflets and an occluder coupled to the prosthetic heart valve, the occluder being configured and arranged to impede the flow of blood clots from the left atrial appendage to the left atrium.

In some embodiments, a method of deploying a heart treatment device at a target site, the heart treatment device including a valve corrector for restoring proper function to a native mitral valve, an occluder and a connector interconnecting the valve corrector and the occluder, includes the steps of: (i) introducing a delivery device to the left atrium, the delivery device including an outer shaft, a plunger, an inner rod disposed within the outer shaft and translatable relative to the outer shaft, and a hook disposed on a distal end of the inner rod, (ii) advancing the plunger to deploy the occluder from, (iii) the outer shaft at the site of the left atrial appendage, (iv) withdrawing the outer shaft toward the interatrial septum to deploy the valve corrector adjacent the native mitral valve; (v) positioning the valve corrector at the native mitral valve to restore proper function to the native mitral valve, and (vi) removing the delivery device from the left atrium.

BRIEF DESCRIPTION OF THE DRAWINGS

Various embodiments of the present invention are disclosed herein with reference to the drawings, wherein:

FIGS. 6A-6E are schematic representations showing a delivery device and the steps of using the delivery device to deploy the heart treatment device of FIG. 3 within a patient;

Various embodiments of the present invention will now be described with reference to the appended drawings. It is to be appreciated that these drawings depict only some embodiments of the invention and are therefore not to be considered limiting of its scope.

DETAILED DESCRIPTION OF THE INVENTION

Blood flows through the mitral valve from the left atrium to the left ventricle. As used herein, the term "inflow," when used in connection with a mitral heart valve, refers to the end of the heart valve closest to the left atrium when the heart valve is implanted in a patient, whereas the term "outflow," when used in connection with a mitral heart valve, refers to the end of the heart valve closest to the left ventricle when a heart valve is implanted in the patient. When used in connection with devices for delivering a heart treatment device into a patient, the terms "trailing" and "leading" are to be taken as relative to the user of the delivery devices. "Trailing" is to be understood as relatively close to the user, and "leading" is to be understood as relatively farther away from the user.

Figure 1:
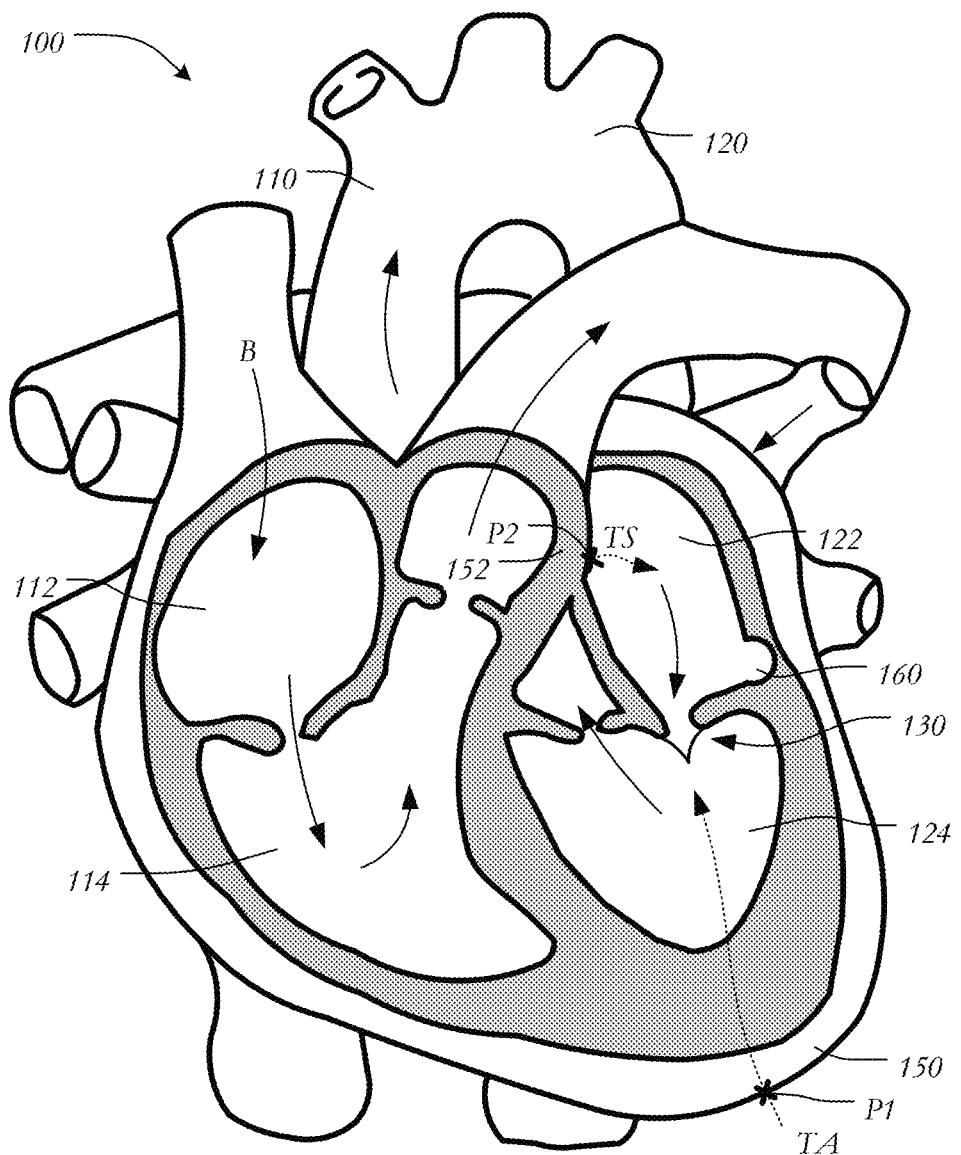
FIG. 1 is a schematic representation of a human heart showing transapical and transseptal delivery approaches.

FIG. 1 is a schematic representation of a human heart 100. The human heart includes two atria and two ventricles: a right atrium 112 and a left atrium 122, and a right ventricle 114 and a left ventricle 124. As illustrated in FIG. 1, the heart 100 further includes an aorta 110, and an aortic arch 120. Disposed between the left atrium and the left ventricle is the mitral valve 130. The mitral valve 130, also known as the bicuspid valve or left atrioventricular valve, is a dual-flap that opens as a result of increased pressure from the left atrium as it fills with blood. As atrial pressure increases above that of the left ventricle, the mitral valve opens and blood passes toward the left ventricle. Blood flows through heart 100 in the direction shown by arrows "B". Adjacent mitral valve 130 is left atrial appendage 160, which empties into left atrium 122.

A dashed arrow, labeled as "TA", indicates a transapical approach for treating or replacing heart tissue. In transapical delivery, a small incision is made between the ribs and into the apex of the left ventricle 124 at position "P1" in heart wall 150 to deliver the prosthetic heart valve to the target site. An alternative path, shown with a second dashed arrow and labeled "TS", indicates a transseptal approach with an incision made through interatrial septum 152 of the heart from the right atrium 112 to the left atrium 122 at position "P2".

Figure 2A:
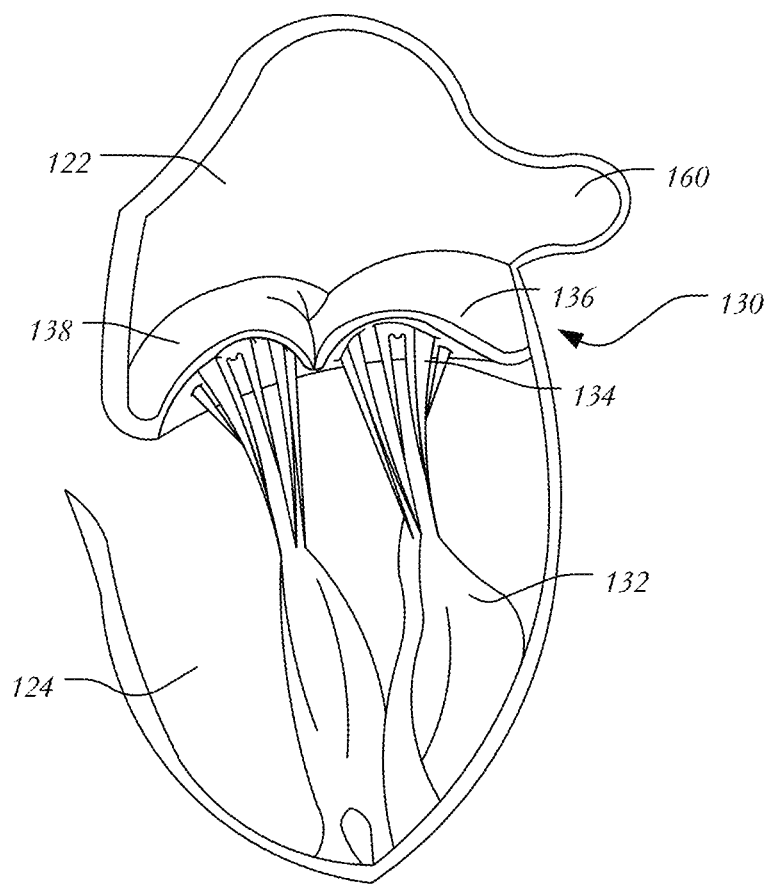
FIG. 2A is a schematic representation of a native mitral valve, a left atrial appendage and associated structures during normal operation.

FIG. 2A is a more detailed schematic representation of native mitral valve 130, left atrial appendage 160 and associated structures. As previously noted, mitral valve 130 includes two flaps or leaflets, posterior leaflet 136 and anterior leaflet 138, disposed between left atrium 122 and left ventricle 124. Cord-like tendons known as chordae tendineae 134 connect the two leaflets 136, 138 to the medial and lateral papillary muscles 132. During atrial systole, blood flows from the left atrium to the left ventricle down the pressure gradient. When the left ventricle contracts in ventricular systole, the increased blood pressure in the chamber pushes the mitral valve to close, preventing backflow of blood into the left atrium. Since the blood pressure in the left atrium is much lower than that in the left ventricle, the flaps attempt to evert to the low pressure regions. The chordae tendineae prevent the eversion by becoming tense, thus pulling the flaps and holding them in the closed position.

During normal function, left atrial appendage 160 contracts rhythmically along with left atrium 122 and blood from left atrial appendage 160 is ejected into left atrium 122, and then passes through mitral valve 130 into left ventricle 124. With each cycle, blood in left atrial appendage 160 is completely emptied out and mitral valve 130 prevents backflow from left ventricle 124 to left atrium 122.

Figure 2B:
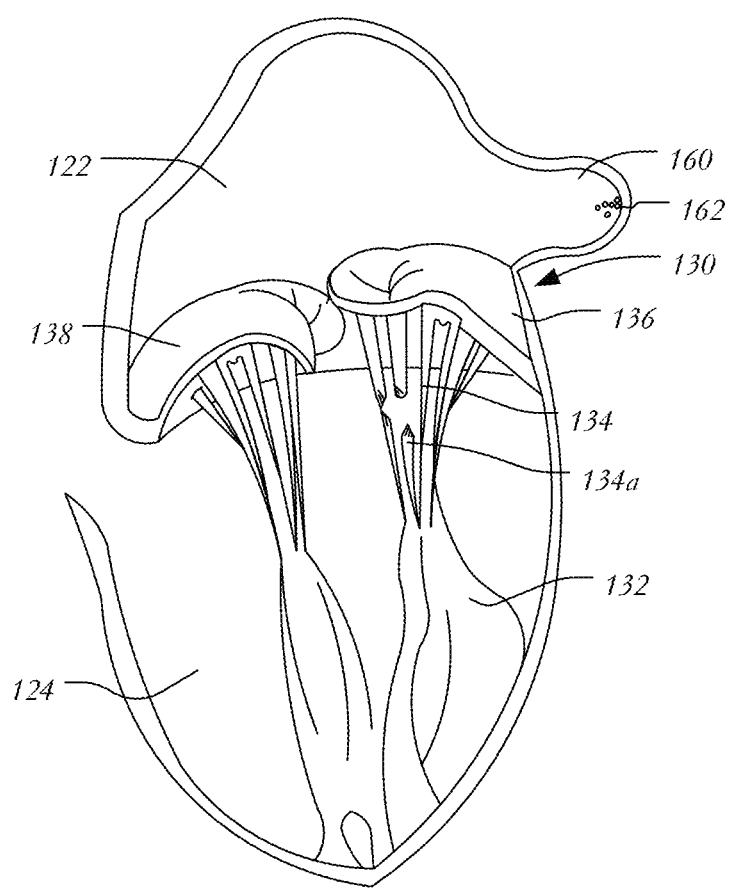
FIG. 2B is a schematic representation of a native mitral valve having a prolapsed leaflet and a left atrial appendage having blood clots.

FIG. 2B is a schematic representation of a malfunctioning heart. First, posterior leaflet 136 has prolapsed into left atrium 122. Moreover, certain chordae tendineae have stretched and others have ruptured. Because of damaged chordae 134a, even if posterior leaflet 136 returns to its intended position, it will eventually resume the prolapsed position due to being inadequately supported. Thus, mitral valve 130 is incapable of functioning properly and blood is allowed to return to left atrium 122 and the lungs. FIG. 2B also illustrates a second malfunction of the heart. In some patients (e.g., older patients), right atrium 112 and left atrium 122 of heart 100 may not beat regularly, a condition known as atrial fibrillation. In some instances, this may result in partial or incomplete ejection of blood from left atrial appendage 160. Stagnant blood in left atrial appendage 160 may form clots 162, which may ultimately travel to the brain and cause a stroke.

Figure 3:
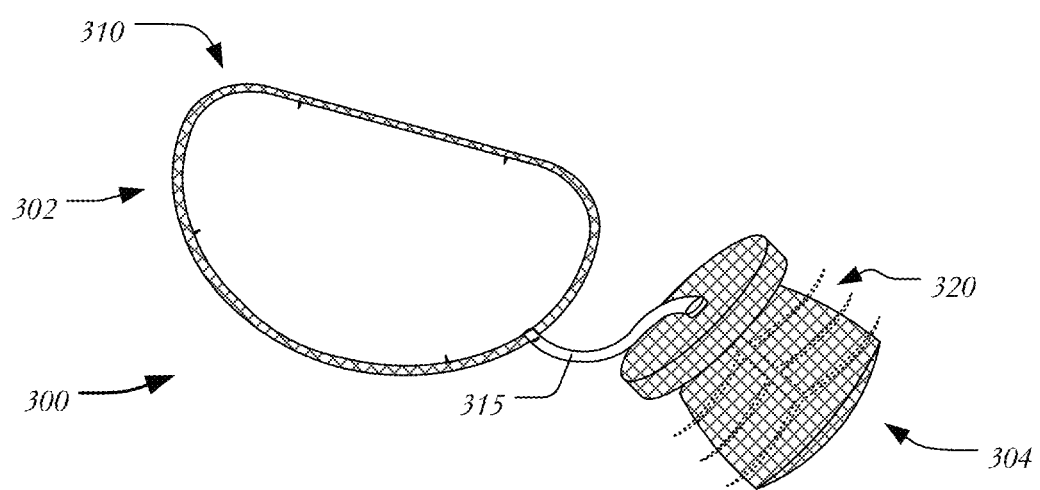
FIG. 3 is a schematic representation of a heart treatment device having a left atrial appendage occluder and an annuloplasty ring.

FIG. 3 is a schematic representation of heart treatment device 300, which is capable of restoring proper function to a malfunctioning mitral valve and reducing the risk of stroke due to atrial fibrillation. Heart treatment device 300 extends between first end 302 and second end 304 and generally includes annuloplasty ring 310 near first end 302 and occluder 320 near second end 304. A connector 315 couples annuloplasty ring 310 to occluder 320 (e.g., one end of connector 315 is attached to annuloplasty ring 310, and the other end of connector 315 is attached to occluder 320). Connector 315 may include a polymer such as polytetrafluoroethylene (PTFE), commonly known by the brand name TEFLON®, or other suitable metallic or polymeric materials that are biocompatible but not biodegradable, such as those used, for example, in making some types of sutures. Additionally, connector 315 may be formed of a shape-memory material so as to define a predetermined spatial relationship between annuloplasty ring 310 and occluder 320. Moreover, though connector 315 is shown as being formed of a single cord, it is not so limited. Thus, it will be understood that connector 315 may include multiple cords that are intertwined with one another or multiple cords that are attached to annuloplasty ring 310 and occluder 320 at different locations. For the sake of clarity, annuloplasty ring 310 and occluder 320 will be described separately with reference to FIGS. 4 and 5.

Figure 4:
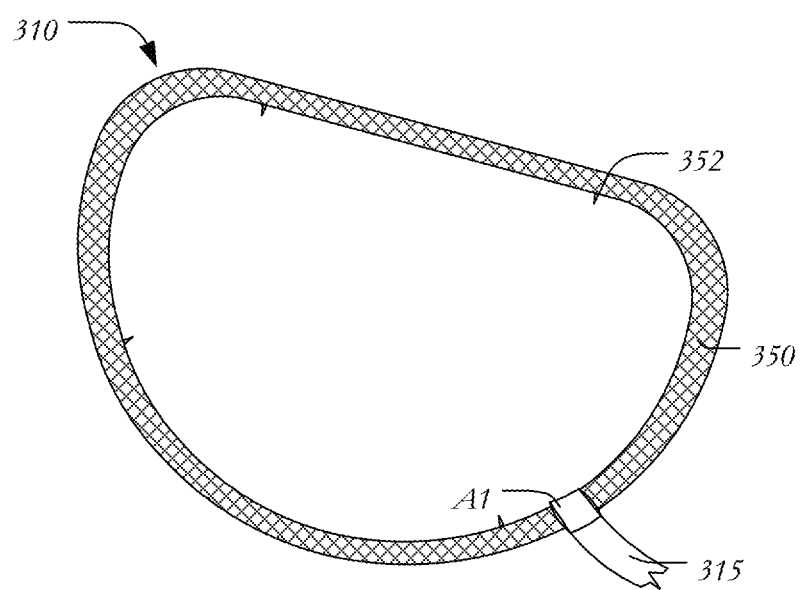
FIG. 4 is an enlarged view of the annuloplasty ring of the heart treatment device of FIG. 3.

Details of annuloplasty ring 310 of heart treatment device 300 are shown in FIG. 4. Annuloplasty ring 310 generally includes body 350 in the form of a ring. As used herein, the term ring does not imply that body 350 is perfectly circular. In fact, body 350 may be oval, saddle-shaped or D-shaped as shown. Moreover, the term ring does not imply that body 350 needs to form a continuous loop. Instead, body 350 may be u-shaped or may form any portion of a loop.

Body 350 may be formed of a plurality of intertwined strands forming a braid which, in the deployed condition, is generally D-shaped as shown. The strands forming the braid may have a predetermined relative orientation with respect to one another (e.g., a helical braid). To prevent unraveling, the ends of the strands may be affixed to one another by any suitable means such as soldering, brazing, welding, gluing, tying, or clamping. Body 350 may comprise a plurality of layers of braided fabric and/or other suitable material such that body 350 is capable of at least partially inhibiting blood flow therethrough in order to facilitate the formation of thrombus and epithelialization. If a braided structure is used, the spacing between strands may be selected so that debris and clots are incapable of passing therethrough.

Body 350 may be formed, for example, of a braided fabric mesh of a shape-memory material, of a super-elastic material, of a bio-compatible polymer, or of another material capable of collapsing and expanding. In the embodiments depicted in FIGS. 3-5, body 350 comprises a braided metal that is both resilient and capable of heat treatment to substantially set a desired preset shape (e.g., the relaxed D-shaped configuration shown in FIG. 3). One class of materials which meets these qualifications is shape memory alloys. One example of a suitable shape memory alloy is Nitinol. It is also understood that body 350 may comprise various materials other than Nitinol that have elastic and/or shape memory properties, such as spring stainless steel, trade named alloys such as Elgiloy® and Hastelloy®, CoCrNi alloys (e.g., trade name Phynox), MP35N®, CoCrMo alloys, or a mixture of metal and polymer fibers. Depending on the individual material selected, the strand diameter, number of strands, and pitch may be altered to achieve the desired properties of body 350.

Optionally, body 350 may include a plurality of fasteners 352 around its perimeter to aid in stabilizing annuloplasty ring 310 about the native mitral valve. FIG. 4 illustrates body 350 having four hook-shaped fasteners 352 spaced about its perimeter and positioned on the interior of body 350 so as to be able to grasp tissue when annuloplasty ring 310 is disposed about a native mitral valve.

Due to the shape-memory properties, body 350 may be collapsed during delivery into the patient and re-expanded after delivery to restore function to the mitral valve. This collapsibility allows body 350 to fit within a small-sized catheter for minimally invasive surgery.

Connector 315 is shown attached to body 350 at position "A1". Position "A1" may be set at one end of body 350 or at any other position on body 350 (e.g., equidistant between two ends of body 350). As seen in FIG. 4, connector 315 may be wrapped around body 350. It will be understood, however, that any suitable method of coupling connector 315 to body 350 may be used, such as an adhesive, sutures, staples and the like.

Figure 5:
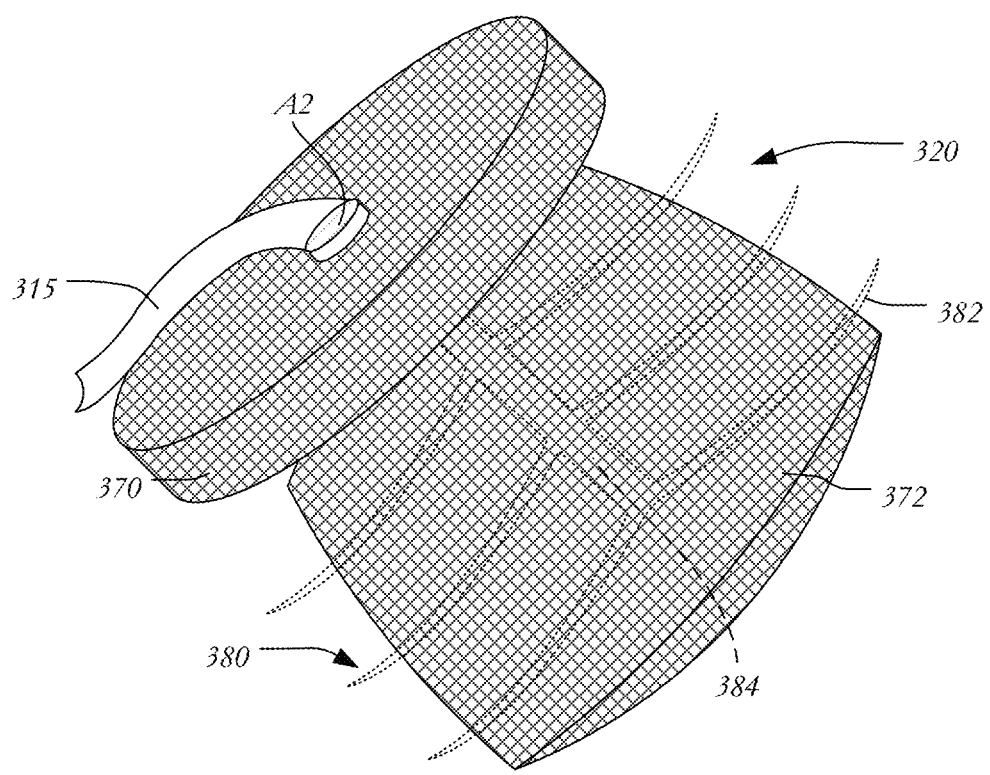
FIG. 5 is an enlarged view of the left atrial appendage occluder of the heart treatment device of FIG. 3.

Details of occluder 320 of heart treatment device 300 are shown in FIG. 5. Occluder 320 includes a pair of bodies 370, 372 formed of any of the materials described above with reference to body 350. As shown, body 370 is disk-shaped while body 372 is basket-shaped. Though bodies 370,372 may be formed of separate portions, it will be understood that a single body may be used having a mushroom shape. Additionally, bodies 370, 372 are shaped and sized to fit within the left atrial appendage 160 when fully expanded, as will be shown below.

Disposed within body 372 is frame 380, which aids in anchoring body 372 within left atrial appendage 160. Frame 380 includes a plurality of tapering ribs 382, each rib 382 extending radially outward from a central spine 384 so as to contact heart tissue. Frame 382 may be formed of a shape-memory material such as Nitinol and configured to be compressed within a delivery device and return to its expanded shape when released from the delivery device. Alternatively, frame 382 may be formed of stainless steel, titanium, Elgiloy®, or a shape-memory polymer (e.g., polyurethanes, polyurethanes with ionic or mesogenic components made by prepolymer method, other block copolymers such as, block copolymers of polyethylene terephthalate (PET), polyethyleneoxide (PEO), block copolymers containing polystyrene and poly(1,4-butadiene), and ABA triblock copolymers made from poly(2-methyl-2-oxazoline) and polytetrahydrofuran).

Connector 315 is coupled to body 370 at position "A2". The method of attachment of connector 315 to body 370 may be similar to that described above with respect to body 350 (e.g., using adhesive, sutures, staples and the like). Alternatively, connector 315 may be connected to spine 384. With connector 315 coupled to both annuloplasty ring 310 and occluder 320, the two portions of device 300 may help to support one another when implanted.

Figure 6A:
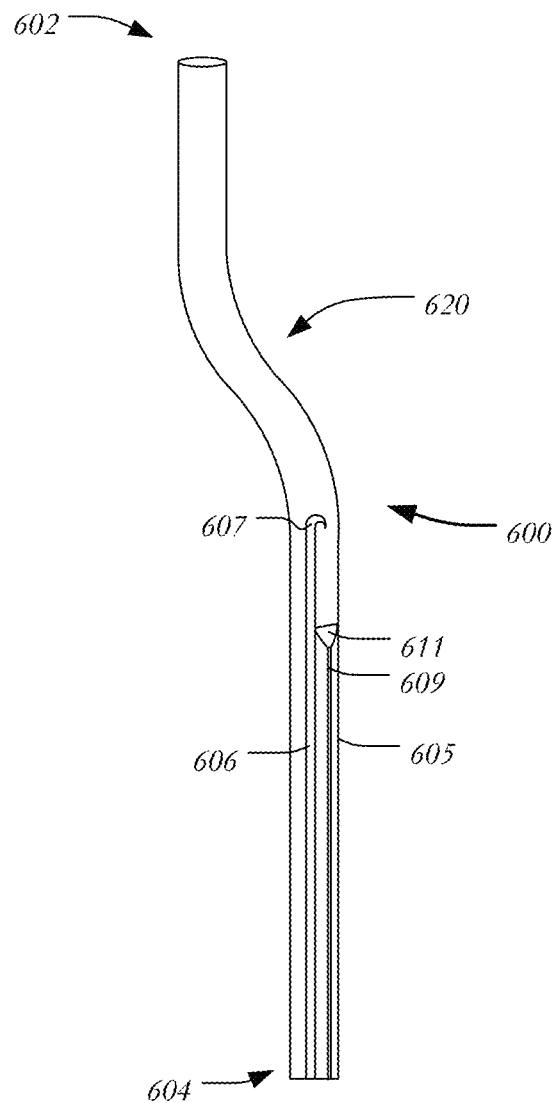

FIG. 6A illustrates a delivery system 600 for delivering heart treatment device 300 to the vicinity of the native mitral valve and deploying annuloplasty ring 310 and occluder 320 at their respective positions. Delivery system 600 extends between leading end 602 and trailing end 604 and includes outer shaft 605 and inner rod 606, inner rod 606 being disposed within outer shaft 605 and translatable relative thereto. Inner rod 606 terminates in hook 607, which is capable of grasping a portion of annuloplasty ring 310 of heart treatment device 300. Alternatively, inner rod 606 may include another structure for coupling with the annuloplasty ring 310 of heart treatment device 300, such as a magnet, screw or other fastener. Outer shaft 605 may have a lumen therethrough that is sized to receive inner rod 606, heart treatment device 300 and a piercing guidewire (not shown) to pierce through tissue, such as, for example, the interatrial septum for transseptal delivery. Optionally, outer shaft 605 may have a curved portion 620 adjacent leading end 602 to aid in delivery. An optional plunger 609 may also be inserted through outer shaft 605 to urge heart treatment device 300 forward through the lumen of outer shaft 605. Plunger 609 may terminate in enlarged head 611 for pushing against a portion of heart treatment device 300. Additionally, both outer shaft 605 and inner rod 606 may be flexible for ease of use.

The use of delivery system 600 to deliver heart treatment device 300 into a patient and deploy same will be described with reference to FIGS. 6B-6G. FIG. 6B illustrates heart treatment device 300 loaded within delivery system 600. In the loaded configuration, heart treatment device 300 is disposed within outer shaft 605 with occluder 320 closest to leading end 602 and annuloplasty ring 310 disposed behind it, and with hook 607 of inner rod 606 coupled to annuloplasty ring 310. Connector 315 is disposed between annuloplasty ring 310 and occluder 320. It will be understood, however, that the illustrated configuration is merely exemplary and that numerous modifications may be made and that certain elements may be rearranged depending on the delivery approach. Transseptal delivery is described herein, although it will be understood that other delivery approaches are possible.

As an initial step, an entry point may be identified at position P2 at interatrial septum 152 for transseptal delivery of delivery system 600 as shown in FIG. 1. An incision may then be made in interatrial septum 152 using a needle or other device to create an entry point and delivery system 600 may be inserted through the entry point into left atrium 122. Delivery system 600 may then be advanced through left atrium 122 to the site of left atrial appendage 160. With leading end 602 of heart treatment device 300 disposed in left atrial appendage 160, heart treatment device 300 may be urged forward in the direction of arrow "S1" through outer shaft 605 using plunger 609, as shown in FIG. 6C. For the sake of clarity, the patient anatomy is not shown. As plunger 609 is pushed forward relative to outer shaft 605, occluder 320 begins to deploy out of leading end 602. In this partially deployed state, only a portion of occluder 320 is outside of outer shaft 605, while annuloplasty ring 310 remains within outer shaft 605. Moreover, the portion of occluder 320 that is disposed outside of outer shaft 605 has begun to expand to its relaxed condition. With continued deployment the entirety of occluder 320 will be exposed outside of outer shaft 605 and will expand within left atrial appendage 160 while annuloplasty ring 310 remains at least partially inside of the outer shaft. When occluder 320 expands, frame 380 also expands and ribs 382 latch onto the tissue of left atrial appendage 160, effectively creating a filter at the opening of left atrial appendage 160.

With occluder 320 in place, the surgeon's attention may turn to annuloplasty ring 310. Outer shaft 605 may be retracted to deploy annuloplasty ring 310. The frictional engagement of occluder 320 within left atrial appendage 160 will hold the occluder in place, such that the retraction of outer shaft 605 will pull annuloplasty ring 310 out from the outer shaft.

Figure 6D:
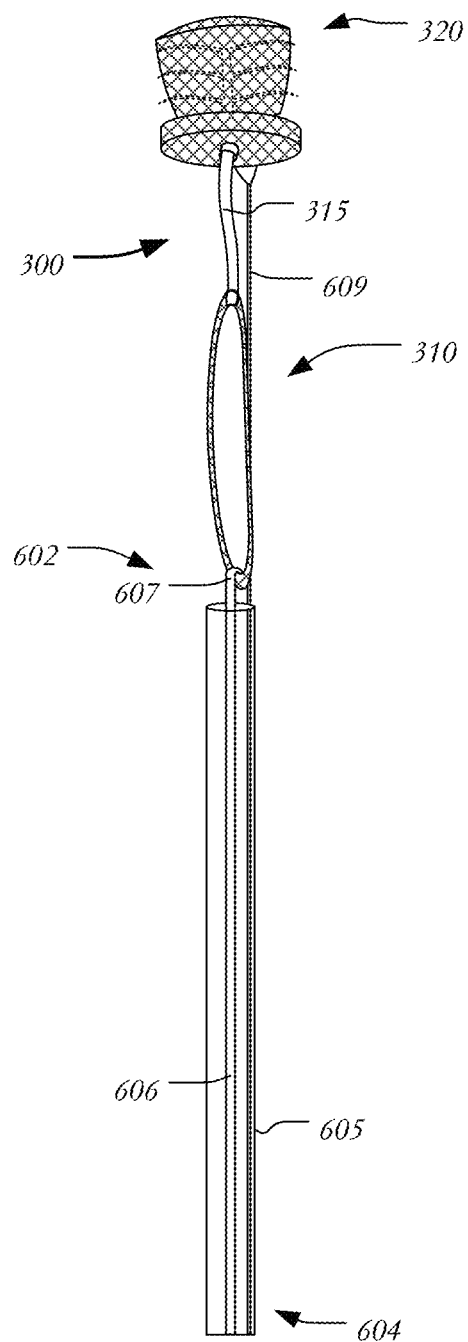
Figure 6E:
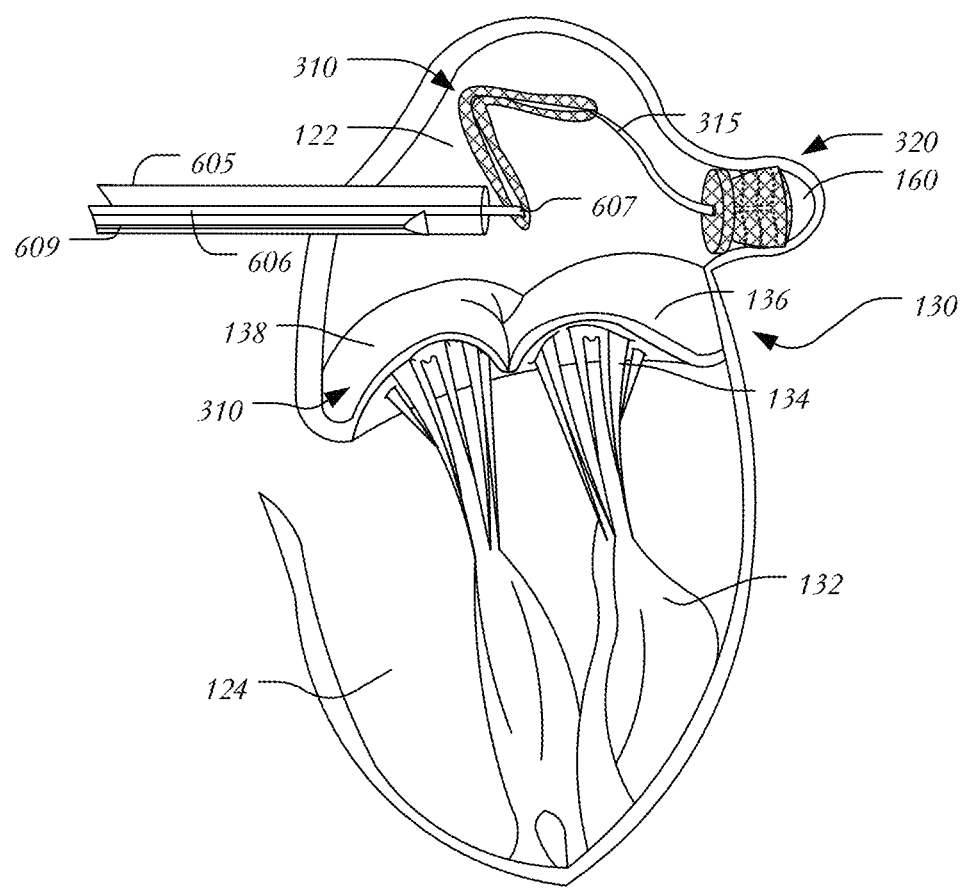

FIGS. 6D and 6E illustrate a fully deployed occluder 320 and annuloplasty ring 310. Hook 607 remains coupled to annuloplasty ring 310, which allows the user to pull heart treatment device 300 back within outer shaft 605 if alignment or positioning is found to be improper. After annuloplasty ring 310 has been deployed from outer shaft 605, it may be manipulated with hook 607 or with a separate wire or other tool and fitted around mitral valve 130 to restore proper function to the mitral valve. Such separate manipulating tool may be advanced to the mitral valve through outer shaft 605 of delivery device 600.

Figure 7:
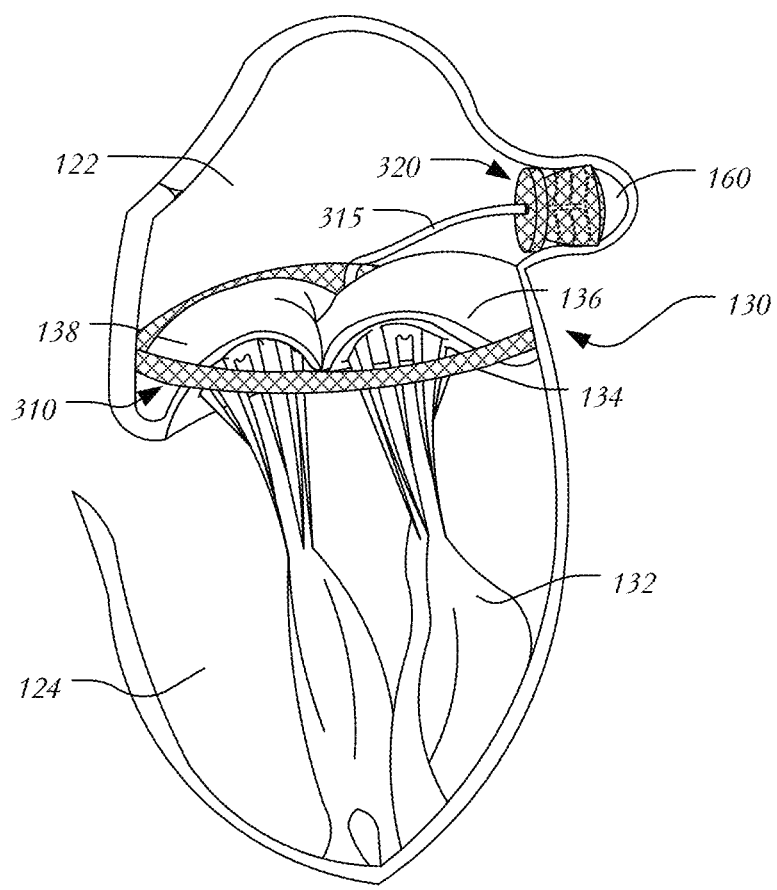
FIG. 7 illustrates the final placement of the heart treatment device of FIG. 3 after anchoring the occluder and the annuloplasty ring.

FIG. 7 illustrates a fully deployed heart treatment device 300 with annuloplasty ring 310 friction fit about mitral valve 130 and occluder 320 secured within left atrial appendage 160. Delivery system 600 has now been completely removed from the heart. Connector 315 extends from annuloplasty ring 310 to occluder 320. Annuloplasty ring 310 may reshape the periphery of mitral valve 310 in order to improve valve function. Additionally, annuloplasty ring 310 may endothelialize and stop any aggressive distortion of the mitral valve. With annuloplasty ring 310 in place, posterior leaflet 136 may still move properly to open mitral valve 130 during atrial systole and allow blood to flow from the left atrium to the left ventricle. However, leaflets 136, 138 may now properly close to prevent regurgitation of blood back into the left atrium, allowing the mitral valve to function as intended as a one-way valve. Moreover, occluder 320 may capture any debris or clots formed in left atrial appendage 160 and prevent stroke. When occluder 320 is firmly anchored within left atrial appendage 160, connector 315 may help keep annuloplasty ring 310 in place. It will be understood that in certain variations, annuloplasty ring 310 may be sutured onto the periphery of mitral valve 130.

Figure 8:
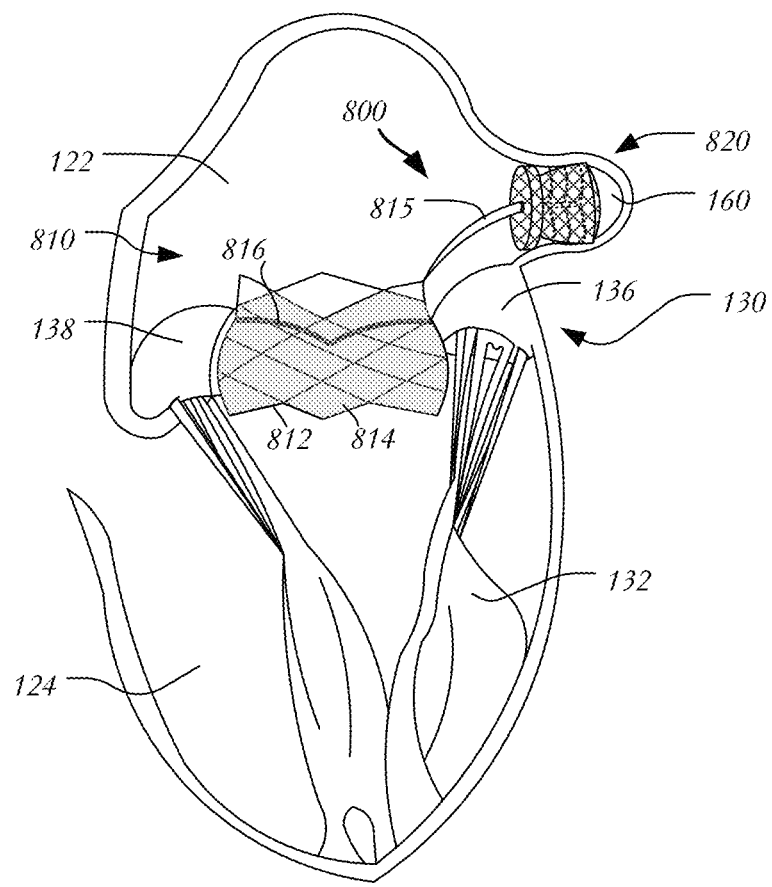
FIG. 8 illustrates another embodiment of a heart treatment device having a left atrial appendage occluder and a prosthetic mitral valve.
Figure 9:
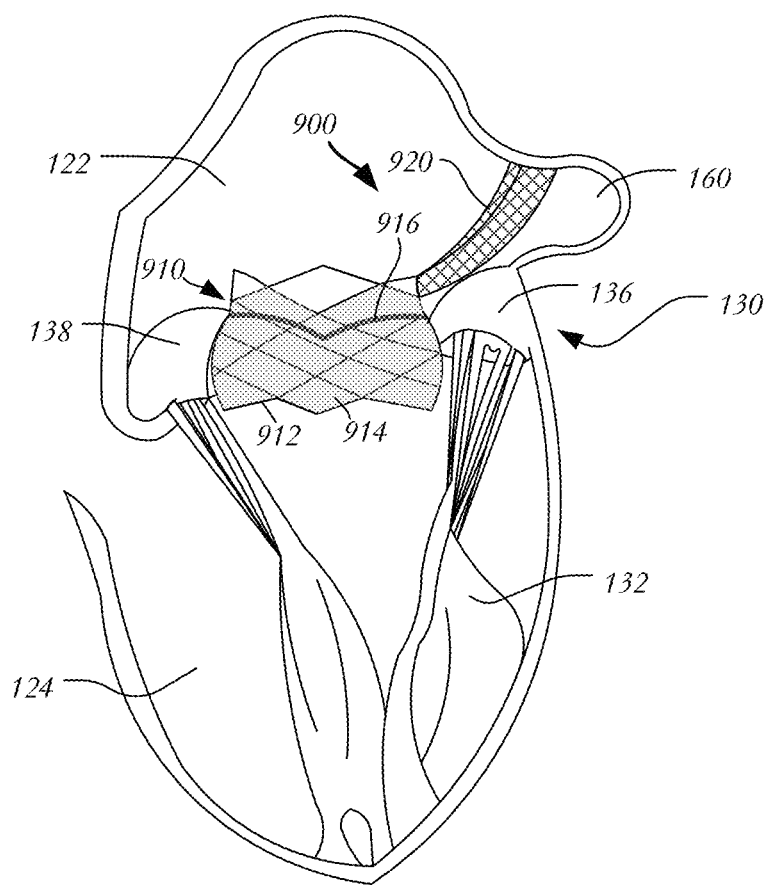
FIG. 9 illustrates another embodiment of a heart treatment device having a left atrial appendage occluder and a prosthetic mitral valve.

Two variations of a heart treatment device are presented in FIGS. 8-9. In FIG. 8, heart treatment device 800 includes a prosthetic mitral valve 810, an occluder 820 and a connector 815 connecting these elements to one another. Connector 815 and occluder 820 may be formed as described above. Instead of an annuloplasty ring, however, a prosthetic mitral valve 810 may be used to replace the function of the native mitral valve. Prosthetic mitral valve 810 may include a compressible and expandable stent 812 and a cuff 814 disposed on the luminal or abluminal surface of a portion of stent 812. Disposed within cuff 814 are a plurality of leaflets 816. Two, three or more leaflets 816 may be used to replace the function of the native leaflets and form a one-way valve to allow blood to flow from left atrium 122 to left ventricle 124. Thus, when an annuloplasty ring 310 is incapable of restoring proper mitral valve function, a replacement valve may be implanted to assume the function of the mitral valve.

In yet another embodiment, heart treatment device 900, shown in FIG. 9, may include prosthetic heart valve 910 and shield 920. Heart valve 910 may include a stent 912, a cuff 914 and leaflets 916 as described above. Shield 920 may be formed of a shape-memory mesh and may be sized to block the opening of left atrial appendage 160. It will be understood that the shape of shield 920 may vary. For example, shield 920 may be shaped as a disk, a bowl or a basket. Moreover, shield 920 may be connected directly to heart valve 910, may be connected to heart valve 910 via a connector, or may be made integral with heart valve 910. For example, shield 920 may be formed integrally with the material of stent 912 at the inflow end of heart valve 910. The shape and orientation of shield 920 may be preset such that when deployed, shield 920 applies a sufficient force against the tissue of left atrium 122 to cover the opening of left atrial appendage 160 and keep the shield in place. Optionally, shield 920 may incorporate a filler such as polyethylene terephthalate to block flow into the left atrial appendage.

It will be appreciated that the various dependent claims and the features set forth therein can be combined in different ways than presented in the initial claims. For example, a heart treatment device may include more or fewer bodies or more or fewer connectors than described. Furthermore, a frame having ribs may be disposed within annuloplasty ring 310, occluder 320 or both. It will also be appreciated that any of the features described in connection with individual embodiments may be shared with others of the described embodiments.

In some examples, the occluder may include a first body and a second body, the first body having a larger cross-section than the second body. The occluder may further include an expandable frame having a plurality of radially-expandable ribs. The occluder may further include a mushroom-shaped body. A connector may include multiple cords. The occluder may include a shape-memory material that is self-expandable from a collapsed condition during delivery into a patient to a relaxed condition during use in the patient. The occluder may include braided strands. The shape-memory material may be nitinol.

In some examples, a device may further include a connector connecting the prosthetic heart valve to an occluder. The occluder may be a disk-shaped shield. The shield may be configured to cover the opening of the left atrial appendage.

In some examples, a method may include an introducing step including introducing the delivery device through the interatrial septum. The method may further include retracting the occluder back into the outer shaft after deploying the occluder. An advancing step may include deploying the occluder adjacent an opening of the left atrial appendage. The advancing step may further include deploying the occluder within the left atrial appendage. A valve corrector may be an annuloplasty ring and the step of positioning the valve corrector may include positioning the annuloplasty ring about the native mitral valve. The valve corrector may be a prosthetic heart valve and the step of positioning the valve corrector may include expanding the prosthetic heart valve within the native mitral valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A heart treatment device having a first end and a second end opposite the first end, the first and second ends defining a maximum length of the heart treatment device in a collapsed condition in which the heart treatment device is receivable within a delivery device, the heart treatment device comprising:

an annuloplasty ring for a mitral valve being D-shaped and positioned at the first end of the heart treatment device;

an occluder having at least one body and a frame disposed within the at least one body, the occluder being configured and arranged for implantation within a left atrial appendage and positioned at the second end of the heart treatment device; and a single connector extending laterally away from an external surface of the annuloplasty ring toward the left atrial appendage and interconnecting the annuloplasty ring and the occluder, the connector being attached at a first position on the annuloplasty ring, the single connector being the only connector interconnecting the annuloplasty ring and the occluder.

2. The heart treatment device of claim 1, wherein the at least one body includes a first body and a second body, the first body having a larger cross-section than the second body.

3. The heart treatment device of claim 1, wherein the frame is expandable and includes a plurality of radially-expandable ribs.

4. The heart treatment device of claim 1, wherein the at least one body comprises a mushroom-shaped body.

5. The heart treatment device of claim 1, wherein the connector comprises nitinol.

6. The heart treatment device of claim 1, wherein the occluder comprises a shape-memory material that is self-expandable from the collapsed condition during delivery into a patient to a relaxed condition during use in the patient.

7. The heart treatment device of claim 6, wherein the occluder comprises braided strands.

8. The heart treatment device of claim 6, wherein the shape-memory material is nitinol.

9. The heart treatment device of claim 1, wherein, the single connector being connected at only two positions including the first position on the annuloplasty ring, and second position on the at least one body.

10. The heart treatment device of claim 1, wherein the at least one body and the frame are formed of different materials.

11. A heart treatment device having a first end and a second end opposite the first end, the first and second ends defining a maximum length of the heart treatment device in a collapsed condition in which the heart treatment device is receivable within a delivery device, comprising:

an annuloplasty ring for a mitral valve being saddle-shaped and positioned at the first end of the heart treatment device;

an occluder having at least one body and a frame disposed within the at least one body, the occluder being configured and arranged for implantation within a left atrial appendage and positioned at the second end of the heart treatment device; and a single connector extending laterally away from an external surface of the annuloplasty ring toward the left atrial appendage and interconnecting the annuloplasty ring and the occluder, the connector being attached at a first position on the annuloplasty ring, the single connector being the only connector interconnecting the annuloplasty ring and the occluder.

* * * * *